US00PP13264P2

(12) United States Plant Patent
Heims

(10) Patent No.: US PP13,264 P2
(45) Date of Patent: Nov. 19, 2002

(54) LOBELIA PLANT NAMED 'GRAPE KNEE-HI'

(75) Inventor: Daniel M. Heims, Tigard, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/967,089

(22) Filed: Sep. 27, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A. Para
(74) *Attorney, Agent, or Firm*—Klarquist Sparkman, LLP

(57) ABSTRACT

A new and distinct hybrid of Lobelia plant characterized by a dwarf habit, deep purple flowers, and sterility, extending the bloom time.

1 Drawing Sheet

BOTANICAL CLASSIFICATION

Lobelia hybrid.

VARIETY DENOMINATION

'Grape Knee-Hi'.

The present invention relates to a new and distinct hybrid of Lobelia, of the family Lobeliaceae, which originated as a cross between *Lobelia siphilitica* dwarf (seed parent), an unpatented plant and an unnamed and unpatented Lobelia interspecific hybrid (pollen parent).

The new variety has been reproduced only by asexual propagation (divison and tissue culture). Each of the progeny exhibits identical characteristics to the original plant.

This plant is characterized by the following:

1. Dwarf habit.

2. Numerous large, deep purple flowers held over the foliage.

3. Strong, short flowering stems that don't fall over.

4. Sterility

Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows Lobelia 'Grape Knee-Hi' growing in the garden in Canby, Oreg.

DETAILED PLANT DESCRIPTION

The following is a detailed description of he new Lobelia hybrid based on observations of a two-year-old specimen grown in the field in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—38 cm. wide and 56 cm. tall.
- *Form.*—Basal clump.

Leaf:
- *Type.*—Simple.
- *Shape.*—Obovate to oblanceolate.
- *Arrangement.*—Alternate.
- *Length.*—6 to 12 cm.
- *Width.*—3 cm. at the widest part.
- *Margins.*—Irregularly serrulate.
- *Apex.*—Acute to acuminate.
- *Base.*—Attenuate.
- *Texture.*—Setose on the top and mostly on the midrib on bottom side.
- *Venation.*—Pinnate.
- *Petiole length.*—5 cm to sessile, clasping at the base.
- *Petiole texture.*—Ciliate.
- *Petiole color.*—Yellow Green 145C.
- *Color.*—Topside — Between Yellow Green 144A and 146A. Bottom — Between Yellow Green 147C and 146C.

Inflorescence:
- *Type.*—Terminal raceme.
- *Peduncle.*—Height: 64 cm. Diameter: 0.5 cm. Texture: Setose. Color: Yellow Green 144A.
- *Cauline leaves.*—Arrangement: Alternate. Shape: Oblanceolate. Color: Same as basal leaves.
- *Pedicel.*—Length: 0.5 to 1.3 cm. Texture: Setose. Color: Purple-Violet 82B.
- *Flower number.*—18 per raceme.

Flower bud:
- *Size.*—3.3 cm. deep and 0.6 cm. wide.
- *Shape.*—Oblong. Tube-like on bottom ⅓ then constricted and top ovoid with an acute tip.
- *Color.*—Violet 83B.
- *Texture.*—Setose.

Flower:
- *Type.*—Zygomorphic.
- *Shape.*—Bilabiate.
- *Size.*—3.5 cm. deep and 2 cm. wide.
- *Corolla.*—Slit to the base on the upper side, upper two lobes recurve and 1.4 cm long, lower three lobes spreading and 1.5 cm. long.
- *Texture.*—Setose on main veins on outside, otherwise satiny.
- *Color.*—Deep purple. Violet 83A.
- *Calyx.*—5 deeply cut acuminate lobes, linear lanceolate, parted to base on corolla, margins revolute.

*Calyx size.*—2 cm deep and tips spreading 1.4 cm wide.
*Calyx color.*—Yellow Green 144A to 145A lightly edged maroon, Greyed Purple 183A.
*Pistil.*—3 cm. long, purple Violet 82C.
*Stamen number.*—5 in a column around the stigma.
*Filament length.*—2.5 cm
*Anther size before dehiscing.*—0.5 cm
*Pollen color.*—White 155D.
*Bloom period.*—July and August in Canby, Oreg.
*Fragrance.*—None.

Fruit:
*Type.*—Dehiscent capsule.
*Color.*—Tan, Grey Brown 199D.

Seed: None produced.
*Fertility.*—Sterile.

Disease: None observed on plant grown under commercial conditions in Canby, Oreg.

COMPARISONS TO SIMILAR LOBELIA

Compared to Lobelia 'Wildwood Splendor', an unpatented plant, this new cultivated variety has a dwarf habit, doesn't fall over, and is female sterile, extending the bloom time.

Compared to Lobelia 'La Fresca', an upatented plant, this new cultivated variety is shorter and has flowers of dark purple violet rather than a dusky purple.

I claim:

1. A new and distinct hybrid of Lobelia plant substantially as shown and described, characterized by a dwarf habit and deep purple flowers.

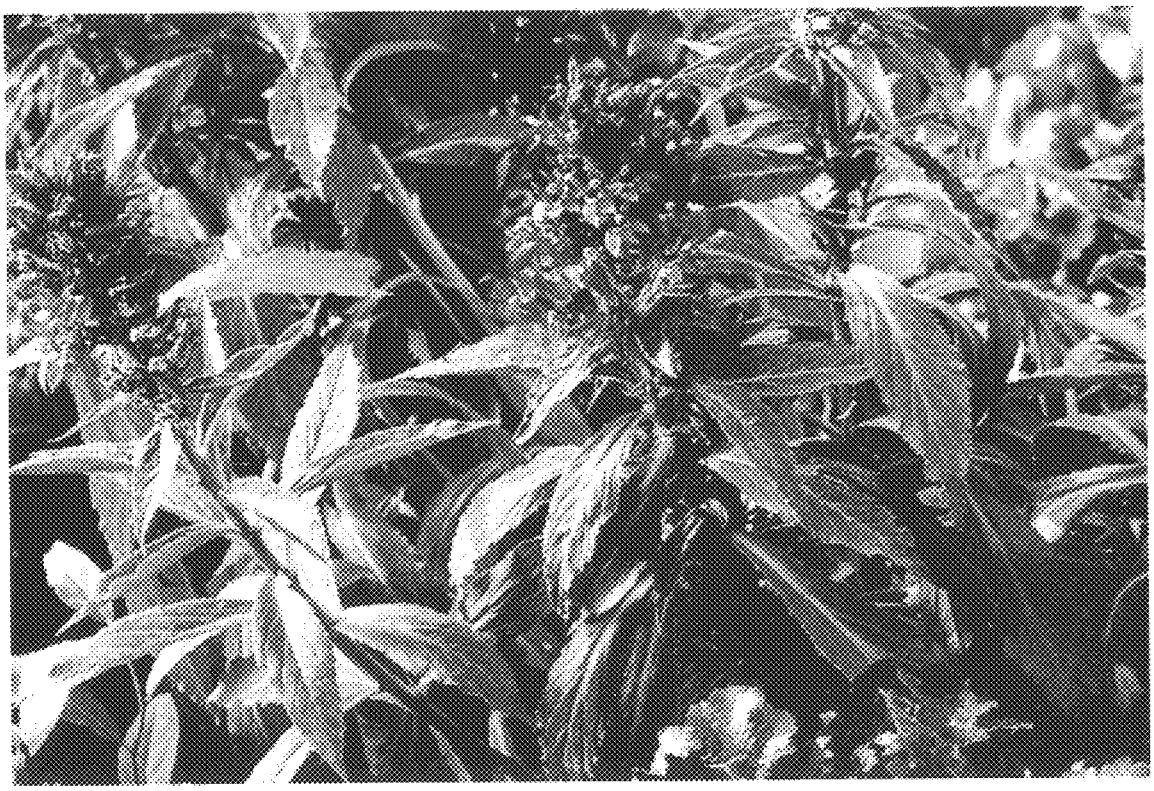

* * * * *